US008746587B2

(12) United States Patent
Soldan et al.

(10) Patent No.: US 8,746,587 B2
(45) Date of Patent: Jun. 10, 2014

(54) VOLATILE MATERIAL DISPENSERS

(75) Inventors: Bridget Soldan, Lisle, IL (US); Jason Gebhardt, Buffalo Grove, IL (US)

(73) Assignee: S.C. Johnson & Son, Inc, Racine, WI (US)

( * ) Notice: Subject to any disclaimer, the term of this patent is extended or adjusted under 35 U.S.C. 154(b) by 654 days.

(21) Appl. No.: 12/761,846

(22) Filed: Apr. 16, 2010

(65) Prior Publication Data

US 2011/0139890 A1 Jun. 16, 2011

Related U.S. Application Data

(60) Provisional application No. 61/286,575, filed on Dec. 15, 2009.

(51) Int. Cl.
A24F 25/00 (2006.01)

(52) U.S. Cl.
USPC .................................................. 239/47; 239/6

(58) Field of Classification Search
CPC .......... B05B 7/24; B05B 7/2459; B05B 15/06
USPC .............................. 239/34, 35, 43, 44, 47, 1, 6
See application file for complete search history.

(56) References Cited

U.S. PATENT DOCUMENTS

| | | | |
|---|---|---|---|
| 3,940,015 A | 2/1976 | Gili | |
| 4,883,049 A | 11/1989 | McDonald | |
| 5,788,155 A | 8/1998 | Martin et al. | |
| 6,102,301 A | 8/2000 | Tiedemann | |
| 6,104,867 A | 8/2000 | Stathakis et al. | |
| 6,431,400 B1 | 8/2002 | O'Maley et al. | |
| 6,569,387 B1 | 5/2003 | Furner et al. | |
| 6,622,662 B1 | 9/2003 | Wolpert et al. | |
| 6,659,301 B2 | 12/2003 | Fellows et al. | |
| 6,766,773 B2 | 7/2004 | Wolpert et al. | |
| 6,768,865 B2 | 7/2004 | Stathakis et al. | |
| D503,621 S | 4/2005 | Heater | |
| 6,889,003 B2 | 5/2005 | Triplett et al. | |
| 7,014,818 B2 | 3/2006 | Rymer | |
| 7,028,861 B2 | 4/2006 | Sayers et al. | |
| 7,157,057 B2 | 1/2007 | Gohil | |
| 7,350,720 B2 * | 4/2008 | Jaworski et al. | ................ 239/55 |
| 7,352,960 B2 | 4/2008 | Hafer et al. | |
| 2004/0195245 A1 | 10/2004 | Gohil | |
| 2005/0194344 A1 | 9/2005 | Heater | |
| 2006/0249593 A1 | 11/2006 | Brown et al. | |
| 2006/0280659 A1 | 12/2006 | Brown et al. | |
| 2008/0099572 A1 | 5/2008 | Tollens et al. | |
| 2009/0127282 A1 | 5/2009 | Reynolds et al. | |
| 2009/0132065 A1 | 5/2009 | Reynolds et al. | |
| 2009/0184173 A1 | 7/2009 | Duru | |

OTHER PUBLICATIONS

PCT/US2011/000680 International Search Report dated Jun. 27, 2011.

* cited by examiner

Primary Examiner — Davis Hwu

(57) ABSTRACT

A volatile material dispenser includes a housing, a retention mechanism coupled to the housing, and a compatible volatile material refill that includes a first set of dimensions and a wick extending therefrom. An adapter is removeably attached to a portion of the compatible volatile material refill. The retention mechanism non-removeably retains the adapter to the housing when the compatible volatile material refill and adapter combination are inserted therein. Further, when the compatible volatile material refill is removed from the adapter, the adapter prevents incompatible volatile material refills having a second set of dimensions different from the first set of dimensions from being attached to the housing.

20 Claims, 12 Drawing Sheets

VOLATILE MATERIAL DISPENSERS

CROSS REFERENCE TO RELATED APPLICATIONS

This application claims the benefit of U.S. Provisional Application Ser. No. 61/286,575, which is incorporated herein in its entirety.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present invention relates generally to volatile material dispensers and, more particularly, to volatile material dispensers that are adapted to be functionally coupled with only specific volatile material refills.

2. Description of the Background of the Invention

Multiple different volatile material dispensers are commercially sold and generally include a housing and a volatile material refill that is inserted into the housing. The refill generally includes a container or bottle for holding a volatile material therein. In some dispensers, the volatile material is passively emitted therefrom. In other dispensers, a diffusion element is utilized to facilitate the dispensing of the volatile material. Examples of diffusion elements include heaters, piezoelectric elements, fans, aerosol actuators, and the like. Regardless of the manner in which the volatile material is emitted, once the volatile material has been expended from the refill, the refill can typically be removed by a user and replaced with a new refill.

One type of commercial volatile material dispenser, referred to herein as a plug-in scented oil dispenser, includes a housing and a heater disposed within the housing. A refill for use with a plug-in scented oil dispenser generally includes a container portion having a bottom end and a top end, wherein the container portion terminates in a neck portion at the top end. A volatile material is disposed within the container portion and a wick is in contact with the volatile material and extends out of the refill through the neck portion. A plug or other connector generally positions and retains the wick within the neck portion. Upon insertion of the refill into the dispenser, at least a portion of the wick is disposed adjacent the heater such that volatile material that moves through the wick is volatilized by the heater.

Another feature of various volatile material dispensers and refills is that each refill has features that are unique or complementary to the particular dimensions of the housing of the dispenser for which it is sold. Still further, each type of dispenser is generally adapted to accept only a single type of refill having features unique or complementary to that dispenser. For example, plug-in scented oil dispensers sold by S.C. Johnson & Son, Inc. ("S.C. Johnson") of Racine, Wis., generally only accept refills sold by S.C. Johnson under their Glade® brand and such refills are designed to fit only within S.C. Johnson plug-in scented oil dispensers. Similarly, plug-in scented oil dispensers sold by Reckitt Benckiser ("Reckitt") of Berkshire, England generally only accept refills sold by Reckitt under their Air Wick® brand and such refills are designed to generally fit only within Reckitt plug-in scented oil dispensers. This is generally the case for most commercial plug-in scented oil dispensers and refills therefor.

In recent years, attempts have been made to create universal refills such that a single refill may interfit with housings of volatile material dispensers sold by multiple different companies under different brands. However, such universal refills can be unwanted, for example, by companies who intend for consumers to purchase only their refills for use with their dispensers. Users may also have developed a preference for specific refills and such universal refills can cause confusion as to the user's preferred company or brand. Further, dispensers may be designed for optimal and safe use with only specific refills.

SUMMARY OF THE INVENTION

According to one embodiment, a volatile material dispenser includes a housing, a retention mechanism coupled to the housing, and a compatible volatile material refill that includes a first set of dimensions and a wick extending therefrom. An adapter is removably attached to a portion of the compatible volatile material refill. The retention mechanism non-removably retains the adapter to the housing when the compatible volatile material refill and adapter combination are inserted therein. Further, when the compatible volatile material refill is removed from the adapter, the adapter prevents incompatible volatile material refills having a second set of dimensions different from the first set of dimensions from being attached to the housing.

According to another embodiment, a method of preventing retention of an incompatible bottle to a volatile material dispenser includes the step of providing a first bottle having a first set of dimensions, a reservoir portion with a volatile material therein, a neck portion extending upwardly from the reservoir portion, and a wick in contact with the volatile material and extending out of the bottle through the neck portion. The method also includes the steps of providing an adapter removably attached to the neck portion of the first bottle, providing a volatile material dispenser including a retention mechanism, and inserting the first bottle with the adapter into the volatile material dispenser so that the retention mechanism fixedly retains the adapter to the housing. Further, the method includes the steps of detaching the first bottle from the adapter and preventing a second bottle from being attached to the volatile material dispenser by the adapter, wherein the second bottle has a second set of dimensions different from the first set of dimensions.

According to yet another embodiment, a method of preventing retention of an incompatible bottle to a volatile material dispenser includes the step of providing a volatile material dispenser including a retention mechanism, wherein the volatile material dispenser is adapted for use with a compatible volatile material refill that includes a bottle having a first set of dimensions and a wick extending therefrom. The method further includes the steps of providing an adapter that is configured to removably attach to a portion of the bottle, non-removably coupling the adapter to the volatile material dispenser by the retention mechanism, and preventing an incompatible volatile material refill from being attached to the volatile material dispenser by the adapter, wherein the incompatible volatile material refill has a second set of dimensions different from the first set of dimensions.

Other aspects and advantages of the present invention will become apparent upon consideration of the following detailed description.

BRIEF DESCRIPTION OF THE DRAWINGS

Other aspects and advantages of the present invention will become apparent upon consideration of the following detailed description, wherein similar structures have like or similar reference numerals.

DETAILED DESCRIPTION

The present disclosure is directed to volatile material dispensers for use with only specific compatible refills. While the present disclosure may be embodied in many different forms, several specific embodiments are discussed herein with the understanding that the present disclosure is to be considered only as an exemplification of the principles of the disclosure, and it is not intended to limit the disclosure to the embodiments illustrated.

Figure 1:
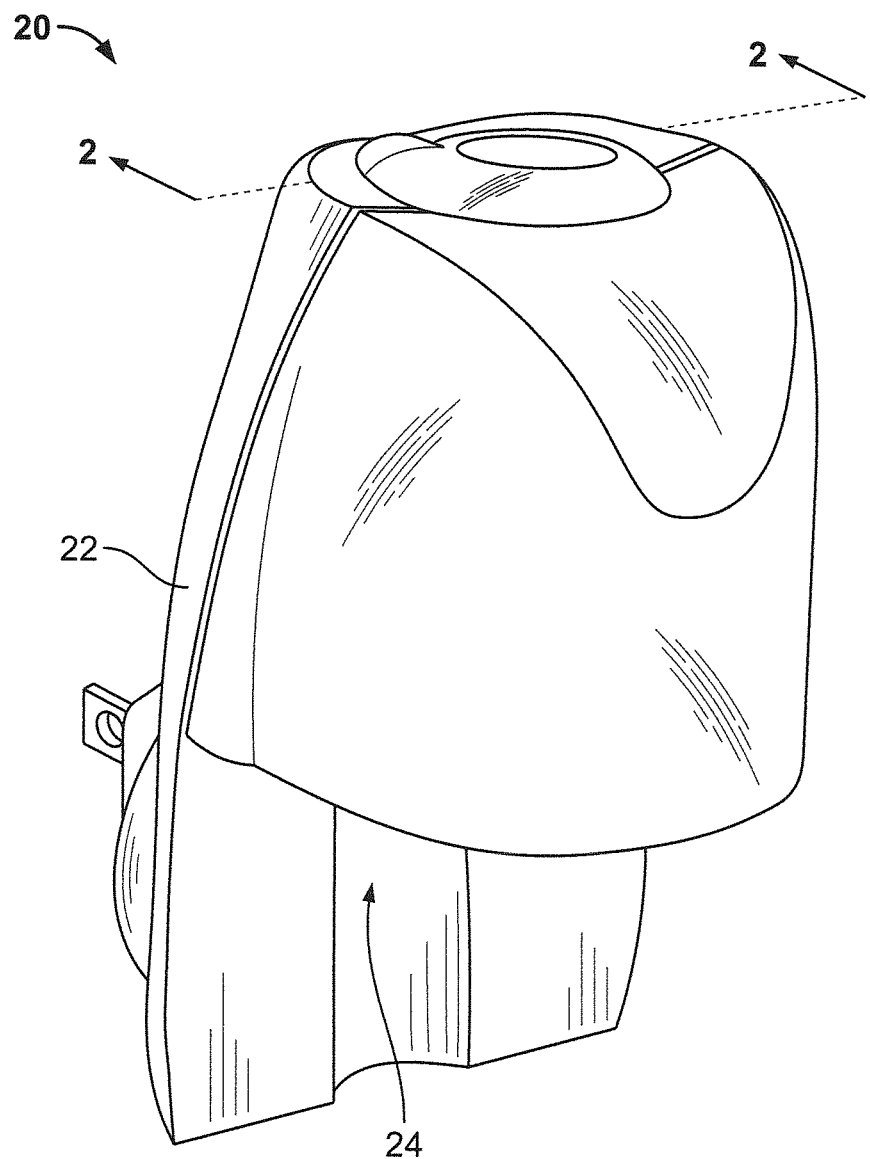
FIG. 1 is a top isometric view of a volatile material dispenser according to one embodiment.
Figure 2:
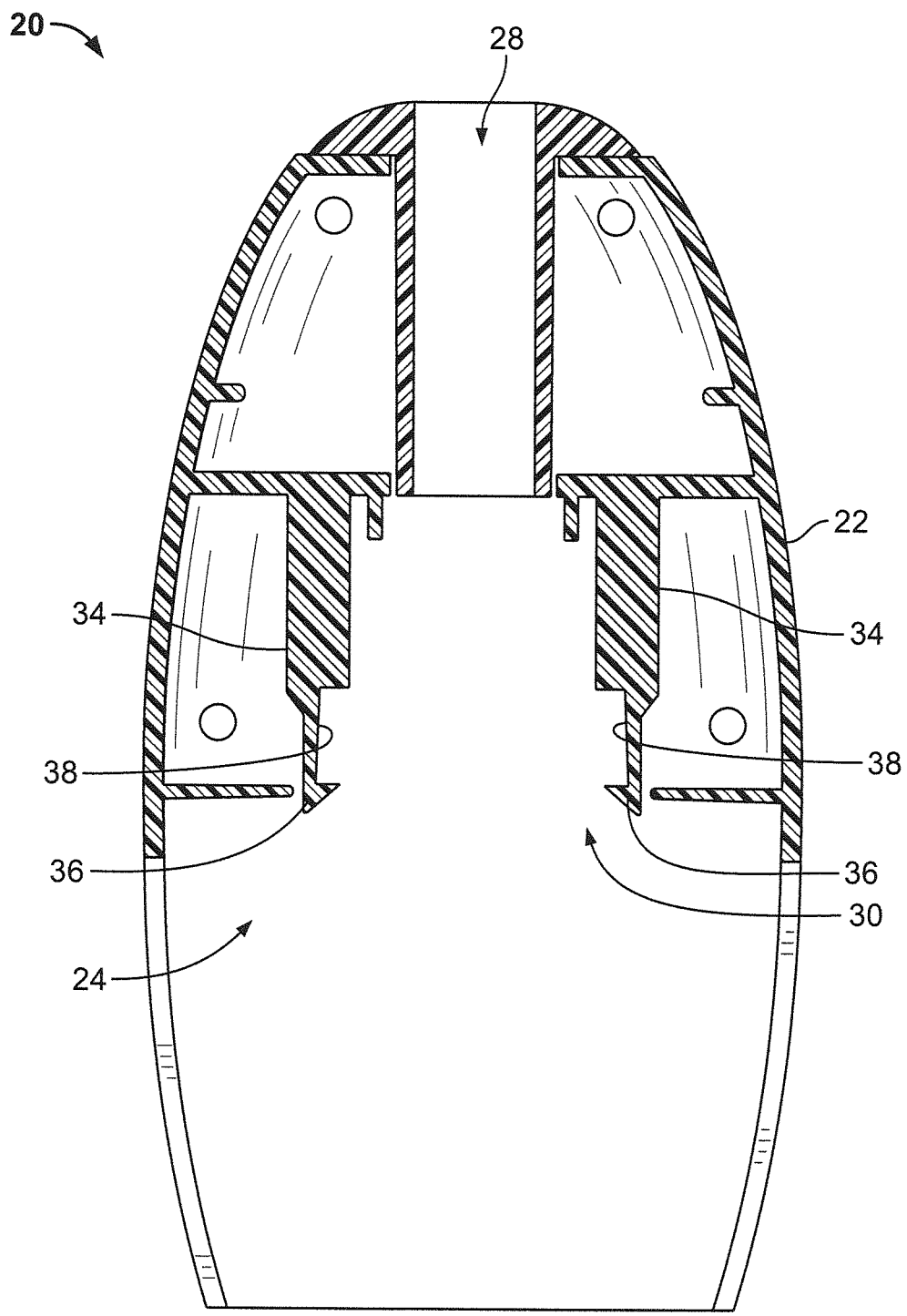
FIG. 2 is a cross-sectional view of the volatile material dispenser of FIG. 1 taken generally along lines 2-2 of FIG. 1.
Figure 3:
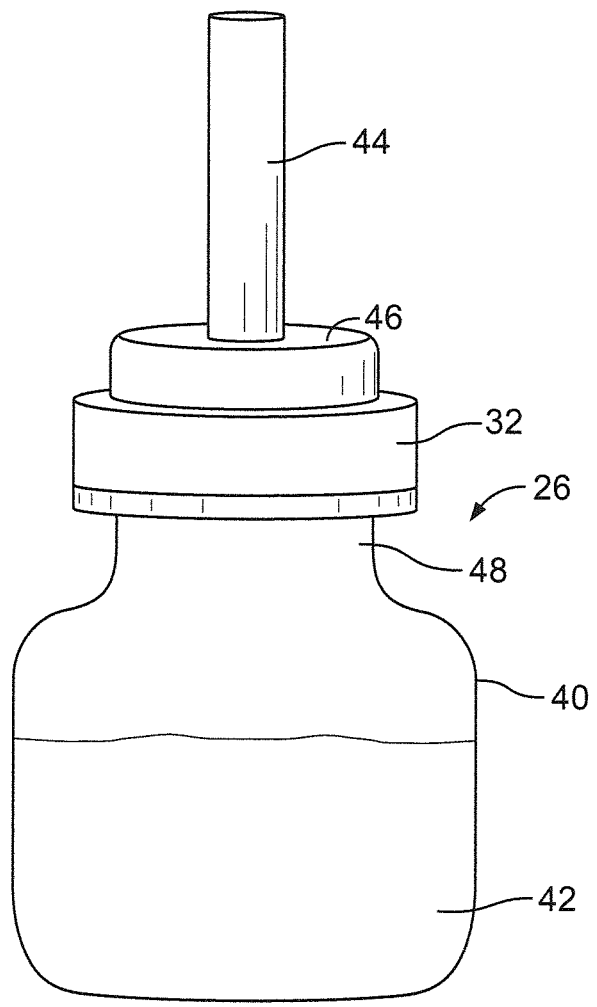
FIG. 3 is a top isometric view of a volatile material refill with a first embodiment of an adapter disposed thereon.

Referring to FIGS. 1-3, a volatile material dispenser 20 includes a housing 22 having a cavity 24 for accepting a compatible volatile material refill 26 and an optional diffusion element (not shown) disposed within the housing. The diffusion element may be a heater, a fan, a piezoelectric element, or any other diffusion element known in the art. The housing 22 further includes a channel 28 for receiving a wick disposed within the refill 26 and a retention mechanism 30 for retaining the refill 26 (or optionally other refills) to the housing 22. Alternatively or in conjunction, the retention mechanism 30 is configured to retain an adapter 32 (FIG. 3) attached to the refill 26 to the housing 22, as will be described in detail hereinafter. The retention mechanism 30, as seen in FIG. 2, includes walls 34 that extend downwardly within the cavity 24 of the dispenser 20. Each of the walls 34 terminates in a latch 36 and may include a notch 38 disposed proximate the latch. The latches 36 and notches 38, in one embodiment, are configured to fixedly retain the adapter 32 of the refill 26. Optionally, the latches 36 alone may retain the adapter 32, and thus the refill 26.

Referring now to FIG. 3, the refill 26 of the present embodiment includes a bottle or container 40 with a volatile material 42 disposed therein. The volatile material 42 disposed in the container 40 may be of any type of volatile material adapted to be dispensed into the air. For example, the volatile material 42 may be a cleaner, an insecticide, an insect repellant, an insect attractant, a mold or mildew inhibitor, a fragrance, a disinfectant, an air purifier, an aromatherapy scent, an antiseptic, a positive fragrancing volatile material, an air-freshener, a deodorizer, or the like, and combinations thereof. Additives may be included in the volatile material, such as, for example, fragrances, and/or preservatives.

An elongate wick 44 is in contact with the volatile material 42 in the container 40 and extends from the container 40 so that at least a portion of the wick 44 is exposed to the ambient environment. A plug assembly 46 holds the wick 44 in place with respect to the container 40. The wick 44 is depicted as a substantially uniform cylinder with a substantially constant diameter throughout the entire length thereof. However, in other embodiments, the wick 44 may be other shapes and sizes as known in the art. The wick 44 may be made of one material or alternatively may be made of multiple materials, e.g., polymeric or porous materials and/or any other material known in the art that are suitable for wicking. The adapter 32 of FIG. 3 is further removably attached to a neck portion 48 of the container 40 by a threaded connection, a frangible portion, adhesive, a bayonet coupling, an interference fit, or any other means that would be apparent to one of skill in the art. In other embodiments, the adapter 32 can be attached to other portions of the container without departing from the spirit of the present invention.

Figure 4:
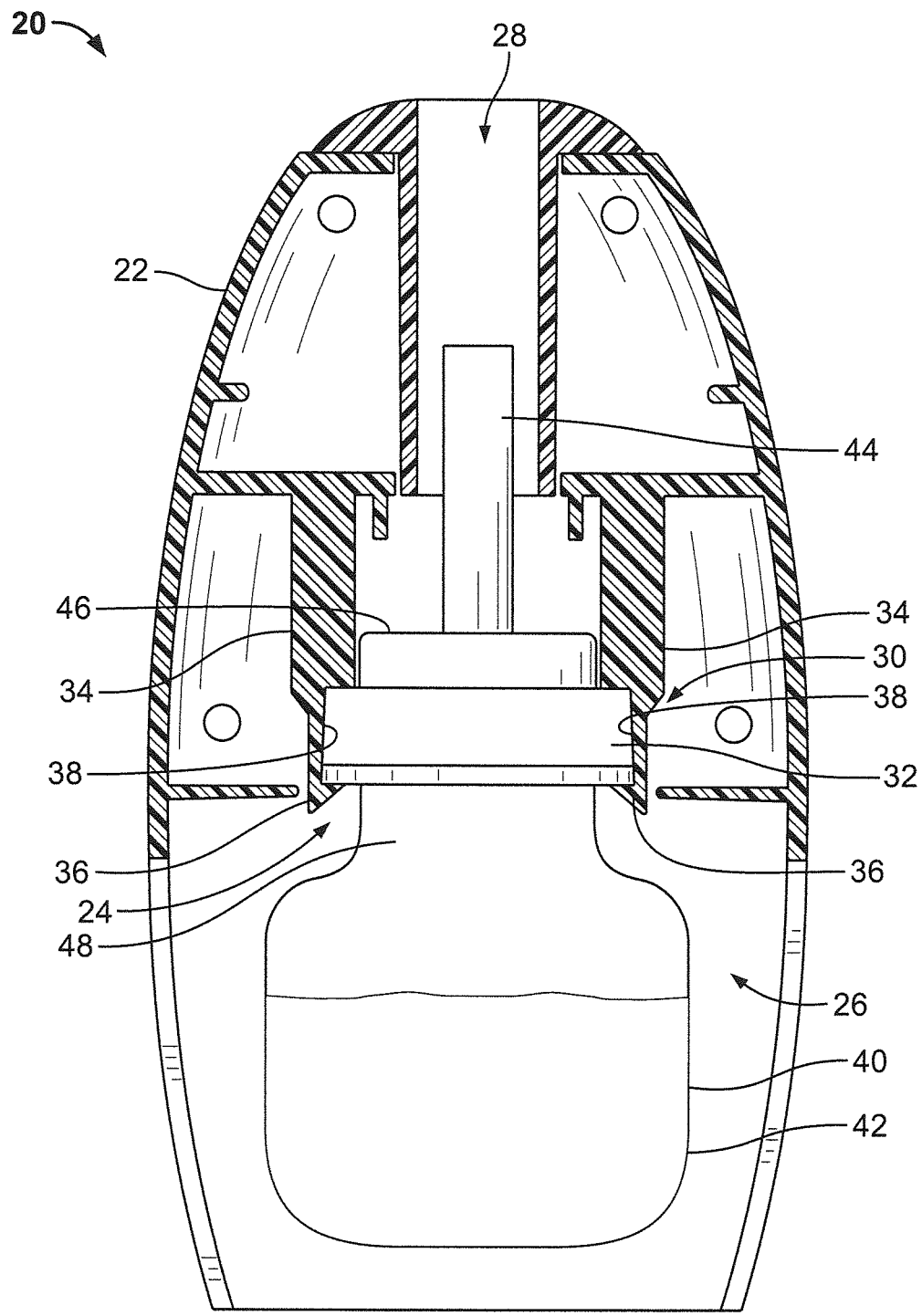
FIG. 4 is a partial cross-sectional view of the volatile material dispenser taken generally along the lines 2-2 of FIG. 1 with an isometric illustration of the volatile material refill of FIG. 3 disposed therein.
Figure 5:
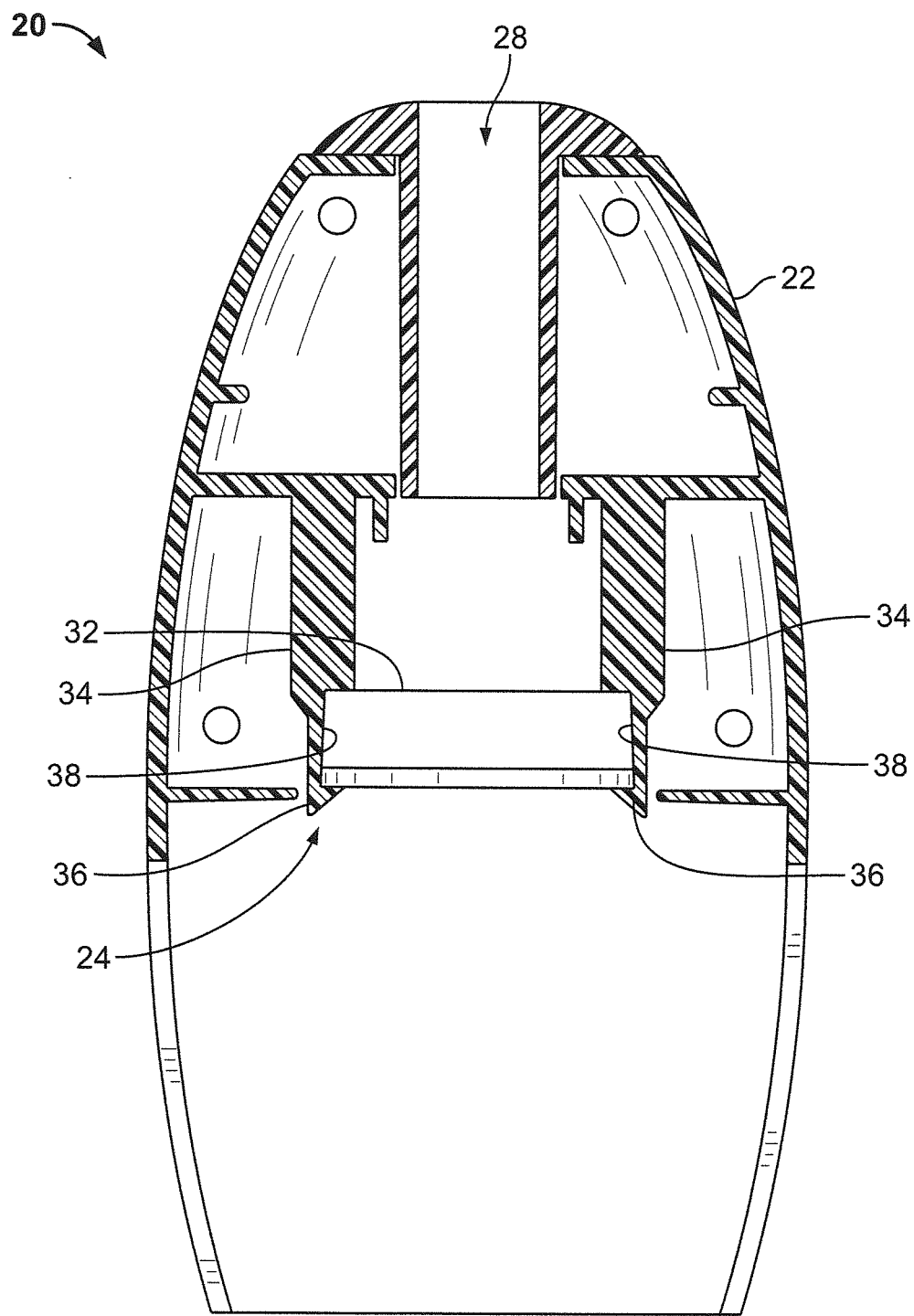
FIG. 5 is a partial cross-sectional view similar to FIG. 4 of the volatile material dispenser with portions of the volatile material refill removed, leaving behind the adapter that is retained within the volatile material dispenser.

FIG. 4 shows that the refill 26 may be inserted into and used with the dispenser 20 by inserting the wick 44 thereof into the channel 28. Once the wick 44 is aligned within the channel 28, the refill 26 is moved upwardly into the dispenser 20 and the latches 36 move outwardly to accommodate the adapter 32. As the adapter 32 passes the latches 36, the latches return to their original position and interfere with the adapter 32 so that the adapter 32 is disposed within the notches 38 and retained by the latches 36. If the notches 38 are not utilized, the adapter 32 can be simply retained by an interference fit with the latches 36. In one embodiment, the adapter 32 is non-removably or fixedly attached to the housing 22 of the dispenser 20 by the latches 36 and/or the notches 38. After the refill 26 and the adapter 32 combination are attached to the dispenser 20, at least a portion of the wick 44 is preferably exposed to allow the diffusion element, preferably in the form of a heater, to act upon the wick 44 to evaporate and dispense the volatile material 42 that is moved to the exposed portion of the wick 44 through capillary action. Once the volatile material 42 within the container 40 becomes depleted, a user can replace the refill 26 with a further refill that contains volatile material. In the present embodiment, the refill 26 may be detached from the adapter 32 so that the adapter remains attached to the housing 22, as shown in FIG. 5. In various examples, the refill 26 may be detached from the adapter 32 by unscrewing the refill, exerting a downward force on the refill 26, or otherwise decoupling the refill 26 in any other known method.

Figure 6:
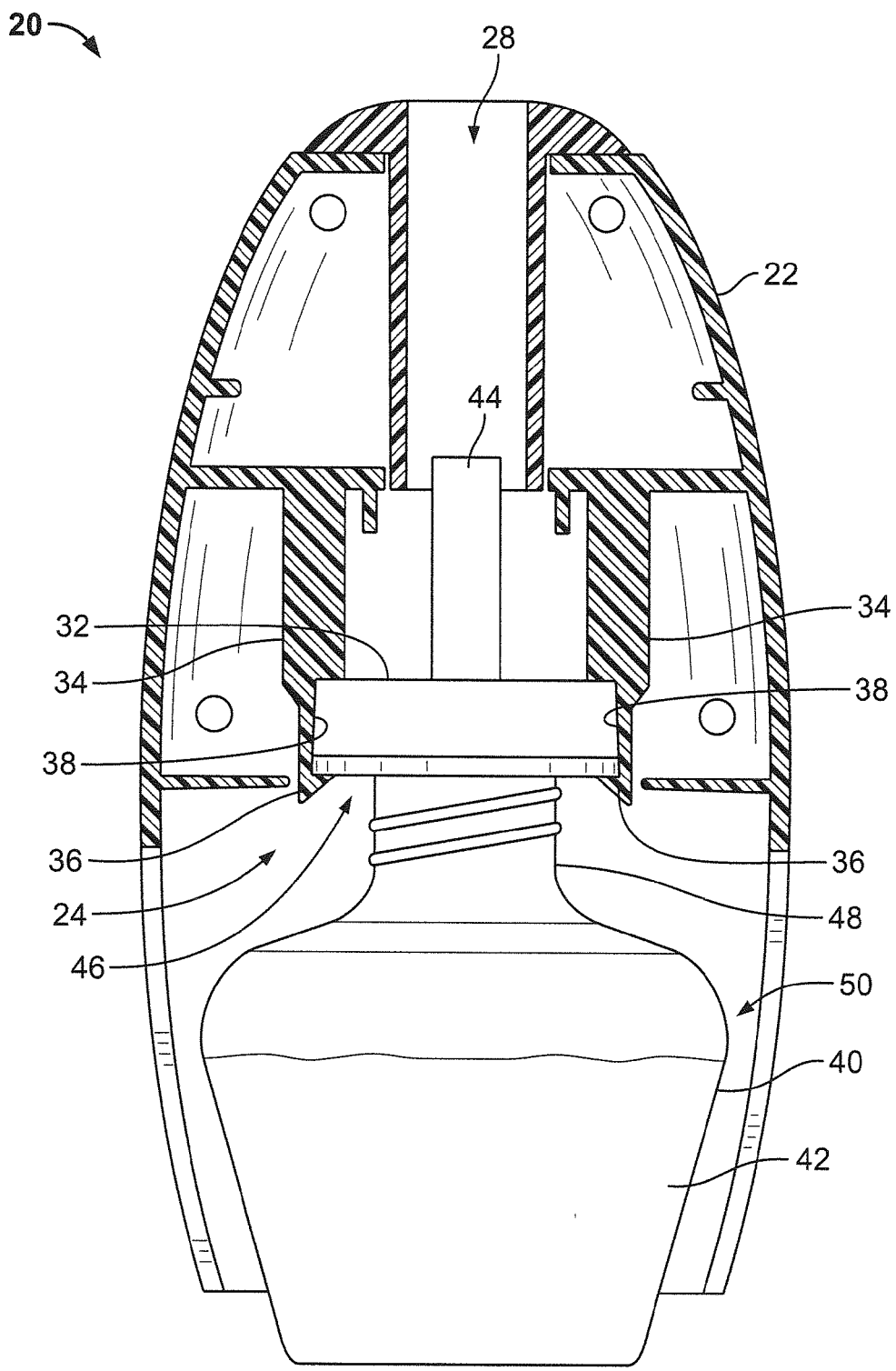
FIG. 6 is a partial cross-sectional view similar to FIG. 5 of the volatile material dispenser with an incompatible volatile material refill.

Subsequently, as shown in FIG. 6, an incompatible second refill 50 that has generally the same components as the refill 26, but has a different configuration, coupling feature(s), and/or dimensions than the refill 26 of FIG. 3, is prevented from being attached to the housing 22 by the adapter 32. In various contemplated embodiments, the adapter 32 can prevent the second refill 50 from being attached to the housing 22 if, for example, the second refill 50 has a neck 48 that is too large or too small, has reverse threading, does not include complementary coupling features, or any other known means. In one embodiment, the second refill 50 would otherwise be capable of being attached to the housing 22 if not for the adapter 32 disposed within the housing. For example, the second refill 50 may include a structure (not shown), for example, threading, one or more projections, and the like, that interferes with the latches 36 to retain the second refill 50 to the housing 22. In the present example, the coupling of the adapter 32 to the housing 22 prevents the latches 36 from retaining the structure or any other portion of the second refill 50, and the adapter 32 prevents attachment of the refill 50, thereby rendering the second refill 50 useless with the dispenser 20.

The adapter 32 can be substantially non-removably attached to the housing 22 so that a user cannot easily remove the adapter 32 without damaging portions of the housing 22. For example, a user can presumably forcefully remove the adapter 32, however, in one embodiment, the walls 34 and/or the latches 36 are designed to fracture if the adapter 32 is forcefully removed therefrom. Consequently, the housing 22 could be rendered incapable of retaining any refill without substantial modifications to the refill and/or housing 22.

Figure 7:
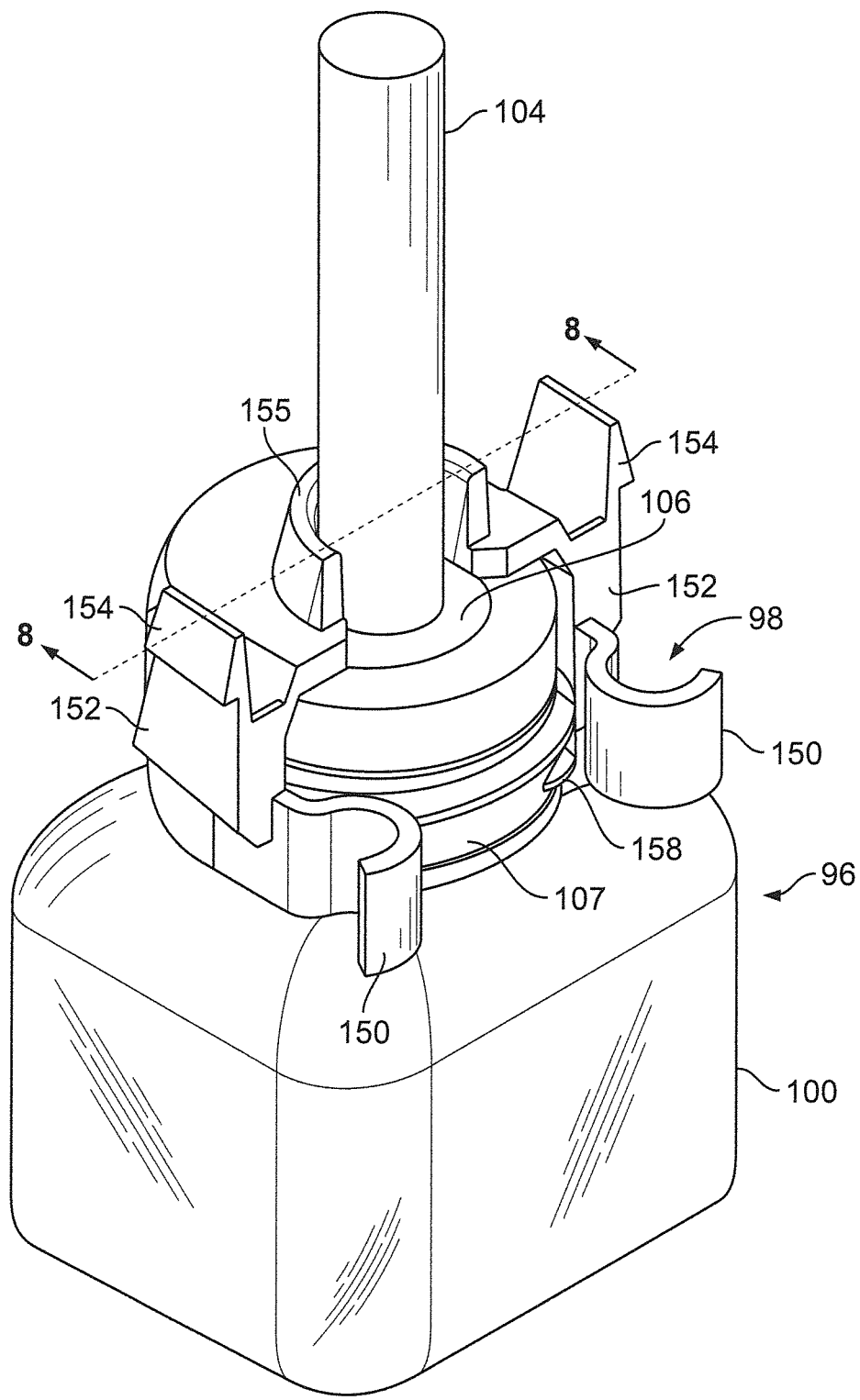
FIG. 7 is a top isometric view of a volatile material refill with further embodiment of an adapter attached thereto.
Figure 8:
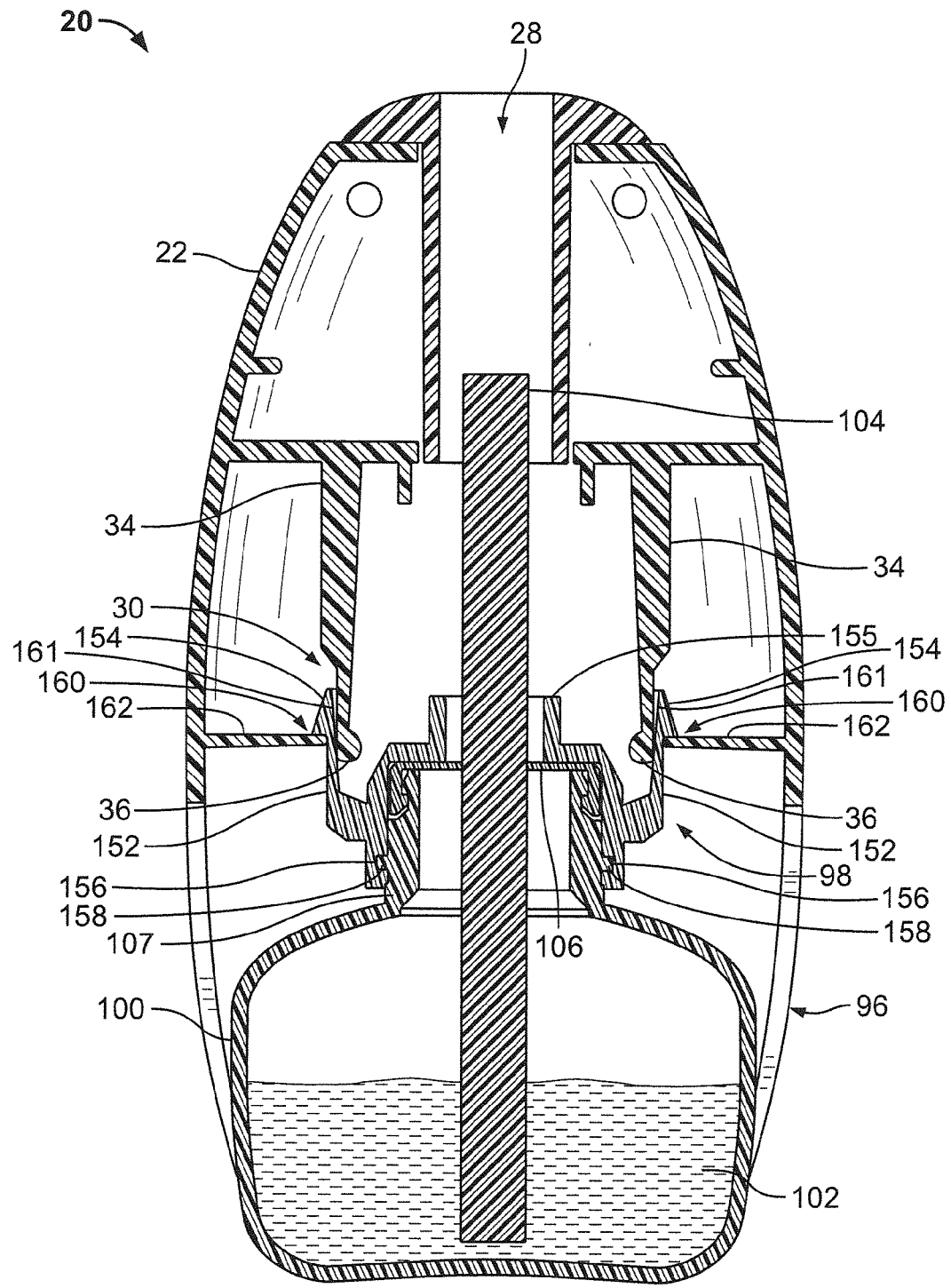
FIG. 8 is a cross-sectional view of the refill of FIG. 7 taken generally along lines 8-8 inserted into a volatile material dispenser similar to the dispenser shown in FIG. 2.

Turning now to FIGS. 7 and 8, a refill 96 is shown with another embodiment of an adapter 98. The refill 96 includes a bottle or container 100 with a volatile material 102 disposed therein. An elongate wick 104 is in contact with the volatile material 102 in the container 100 and extends from the container 100 so that at least a portion of the wick 104 is exposed to the ambient environment. A plug assembly 106 is disposed in a neck portion 107 of the container 100 and holds the wick 104 in place with respect to the container 100.

In the present embodiment, the adapter 98 of FIGS. 7-10 is a substantially semi-circular structure that is removably attached to the refill 96. Although the adapter 98 is disclosed as being semi-circular in shape, any other shaped adapters are possible, as long as the adapter retains the same functions as described herein. The refill 96 may be provided with the adapter 98 affixed thereto, in a package with the adapter 98, or completely separate from the adapter 98. As best seen in FIG. 7, the adapter 98 includes optional opposing resilient outwardly facing C-shaped clasps 150 and upwardly extending latches 152 disposed adjacent the clasps 150. The latches 152 include outwardly extending projections 154, the function of which will be discussed in greater detail hereinafter. An optional semi-cylindrical neck portion 155 extends upwardly from the adapter 98 and can be used to assist in retaining the wick 104 in place once the adapter 98 is inserted onto the refill 96.

Referring to FIG. 8, at least one groove or indentation 156 is disposed on an inner surface of the adapter 98 to aid in retaining the adapter 98 on the container 40. The one or more grooves 156 are configured to correspond to threaded portions 158 of the neck portion 107 of the refill 96. Optionally, other projections (not shown) or indentations may be disposed on the neck portion 107 of the refill 96 for cooperation with portions of the adapter 98 (including grooves therein) to aid in retaining the adapter 98 thereto. The adapter 98 can be made of any suitable material, e.g., polypropylene, polyethylene, high density polyethylene, low density polyethylene, and the like.

In the embodiment of FIGS. 7-10, the adapter 98 is secured to the neck portion 107 of the container 100 by sliding the adapter 98 horizontally around the neck portion 107. Pressure exerted on the adapter 98 is transferred to the neck portion 107, which causes the clasps 150 to flex outwardly until the clasps 150 pass the neck portion 107. Once past the neck portion 107, the clasps 150 return to their original position, wherein the adapter 98 is disposed around and retained on the neck portion 107. As the adapter 98 is positioned on the refill 96, the indentations 156 formed in the adapter interact with the threaded portions 158 (or another feature on the refill 96) to assist in retaining the adapter 98 on the container 100 in a direction generally parallel to the wick 104. The adapter 98 can be removably attached to the container 100 by other means without departing from the spirit of the present invention. For example, the adapter 98 can be attached by an interference fit, a bayonet-type connection, threading, a snap fit, and the like.

Figure 9:
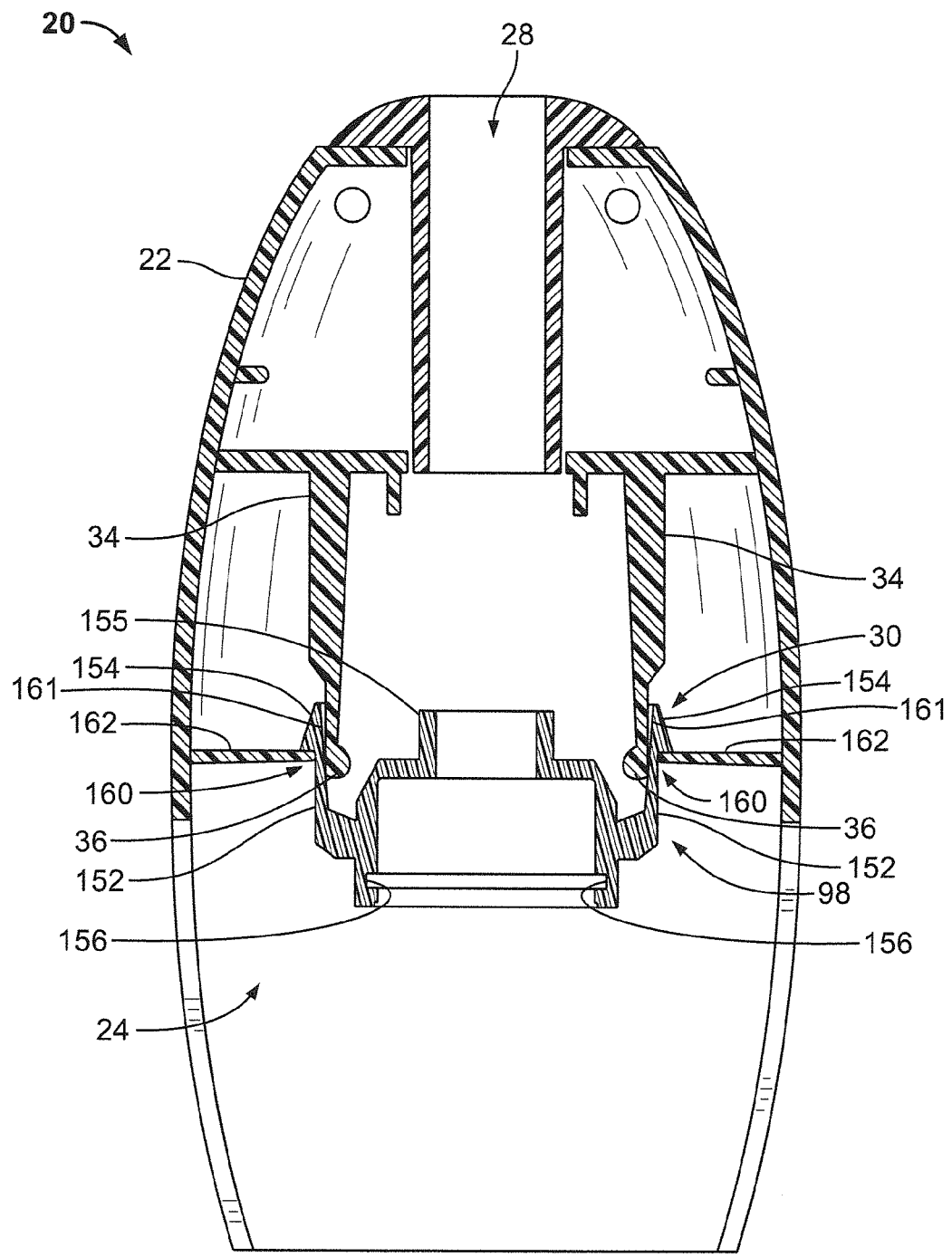
FIG. 9 is a cross-sectional view similar to FIG. 8 of the volatile material dispenser with portions of the volatile material dispenser removed, leaving behind the adapter, which is retained within the volatile material dispenser.

After the adapter 98 is secured to the refill 96, the refill 96 is inserted into the dispenser 20 in the manner shown in FIG. 8. The wick 104 is inserted into the cavity 24 and then the channel 28 of the housing 22 of the dispenser 20. As the refill 96 is inserted into the dispenser 20, the projections 154 extending outwardly from the latches 152 slide through gaps 160 formed between rear surfaces 161 of the resilient latches 36 disposed within the cavity 24 of the dispenser housing 22 and horizontal walls 162 aligned with the latches 36. In particular, the latches 36 flex inwardly to allow the projections 154 to pass through the gaps 160. Once the projections 154 pass through the gaps 160, the latches 152 flex outwardly to prevent downward movement of the projections. In one embodiment, the adapter 98 is non-removeably or fixedly attached to the housing 22 of the dispenser 20 by the projections 154 interfering with the horizontal walls 162. After the refill 96 and the adapter 98 combination is attached to the dispenser 20, at least a portion of the wick 104 is preferably exposed to allow the diffusion element, preferably in the form of a heater, to evaporate and dispense volatile material 102 that is moved to the exposed portion of the wick through capillary action. Once the volatile material 102 within the container 100 becomes depleted, a user can replace the refill 96 with a further refill that contains volatile material. In the present embodiment, the refill 96 may be detached from the adapter 98 so that the adapter 98 remains attached to the housing 22, as shown in FIG. 9. In various examples, the refill 96 may be detached from the adapter 98 by unscrewing the refill 96, exerting a downward force on the refill 96, or otherwise decoupling the refill 96 in any other known method.

Figure 10:
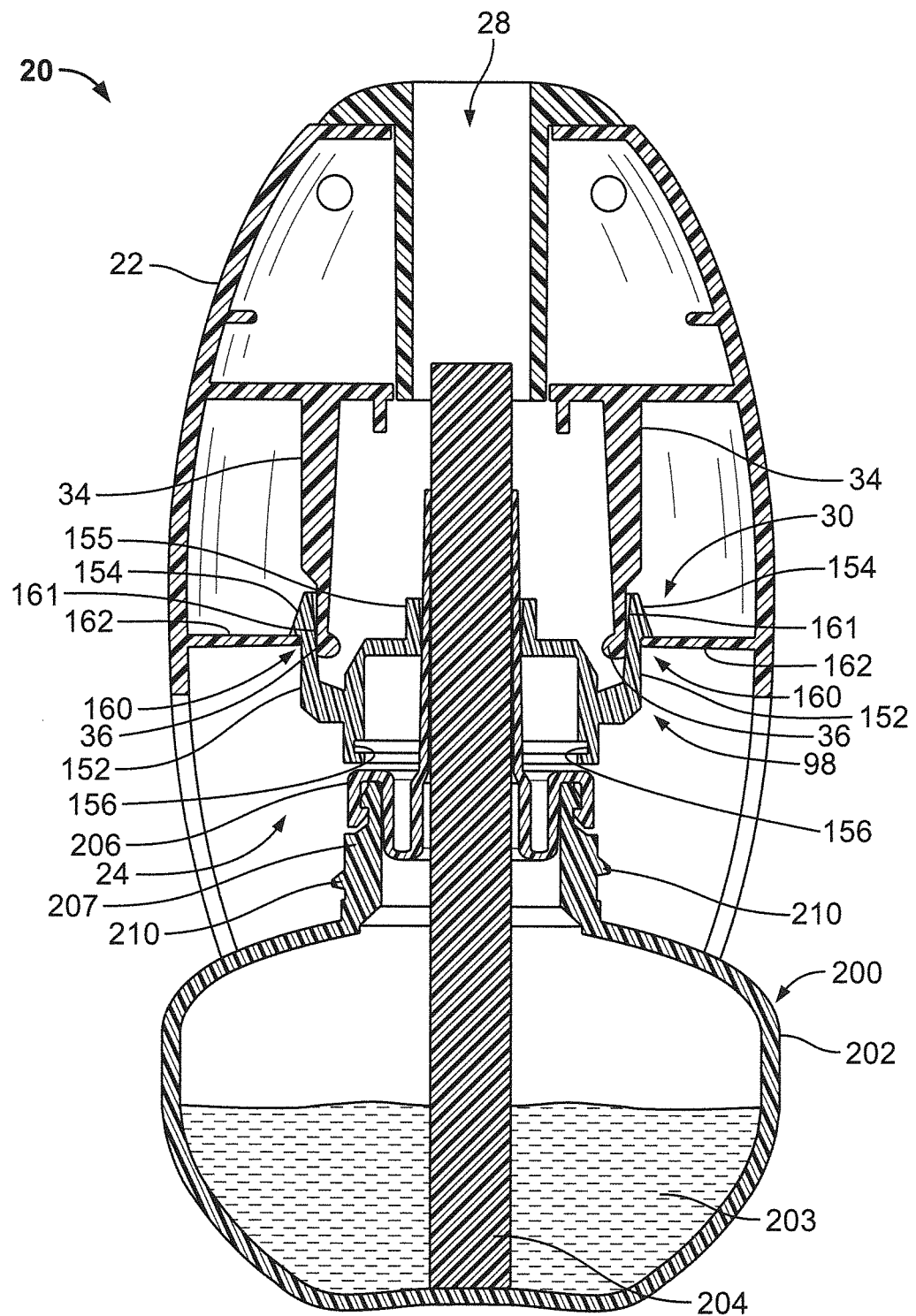
FIG. 10 is a cross-sectional view similar to FIG. 9 of the volatile material dispenser with an incompatible volatile material refill.

Subsequently, as shown in FIG. 10, an incompatible second refill 200 that has generally the same components as the refill 96, but has a different configuration, coupling feature(s), and/or dimensions than the refill 96 of FIG. 7 is prevented from being attached to the housing 22 by the adapter 98. The refill 200 generally includes a bottle or container 202 with a volatile material 203 disposed therein. An elongate wick 204 is in contact with the volatile material 203 in the container 202 and extends from the container 202 so that at least a portion of the wick 204 is exposed to the ambient environment. A plug assembly 206 is disposed in a neck portion 207 of the container 202 and holds the wick 204 in place with respect to the container 202.

In various contemplated embodiments, the adapter 98 can prevent the second refill 200 from being attached to the housing 22 if the second refill 200 has a neck that is too large or too small, has reverse threading, does not include complementary coupling features, or any other known means. In one embodiment, the second refill 200 would otherwise be capable of being attached to the housing 22 if not for the adapter 98 disposed within the housing 22. For example, the second refill 200 may include an annular ring or threading 210 that interferes with the latches 36 to retain the second refill 200 to the housing 22. In the present example, the coupling of the adapter 98 to the housing prevents the latches 36 from retaining the annular ring 210 on the second refill 200. Further, the adapter 98 can be substantially non-removably attached to the housing 22 so that a user cannot easily remove the adapter 98 without damaging portions of the housing 22. For example, a user can presumably forcefully remove the adapter 98, however, in one embodiment, the horizontal walls 162, latches 36, and/or walls 34 are designed to fracture if the adapter 98 is forcefully removed therefrom. Consequently, the housing 22 could be rendered incapable of retaining any refill without substantial modifications to the refill and/or housing 22.

Other embodiments of the adapter 98 of FIGS. 7-10 are contemplated, wherein the adapter 98 may be attached to any portion of the container 100, the neck portion 107, the plug assembly 106, and/or the wick 104. The relevant features of the adapter 98 are a mechanism for attachment to the refill 96 and the latches 152 with outwardly extending projections 154 or other means for non-removably attaching the adapter 130 between the latches 36 and the horizontal walls 162. Various embodiments of the adapter 98 may be attached to a refill in any manner known in the art including, for example, a snap fit, threading, bayonet-type connection, an interference fit, and/or the like.

Figure 11:
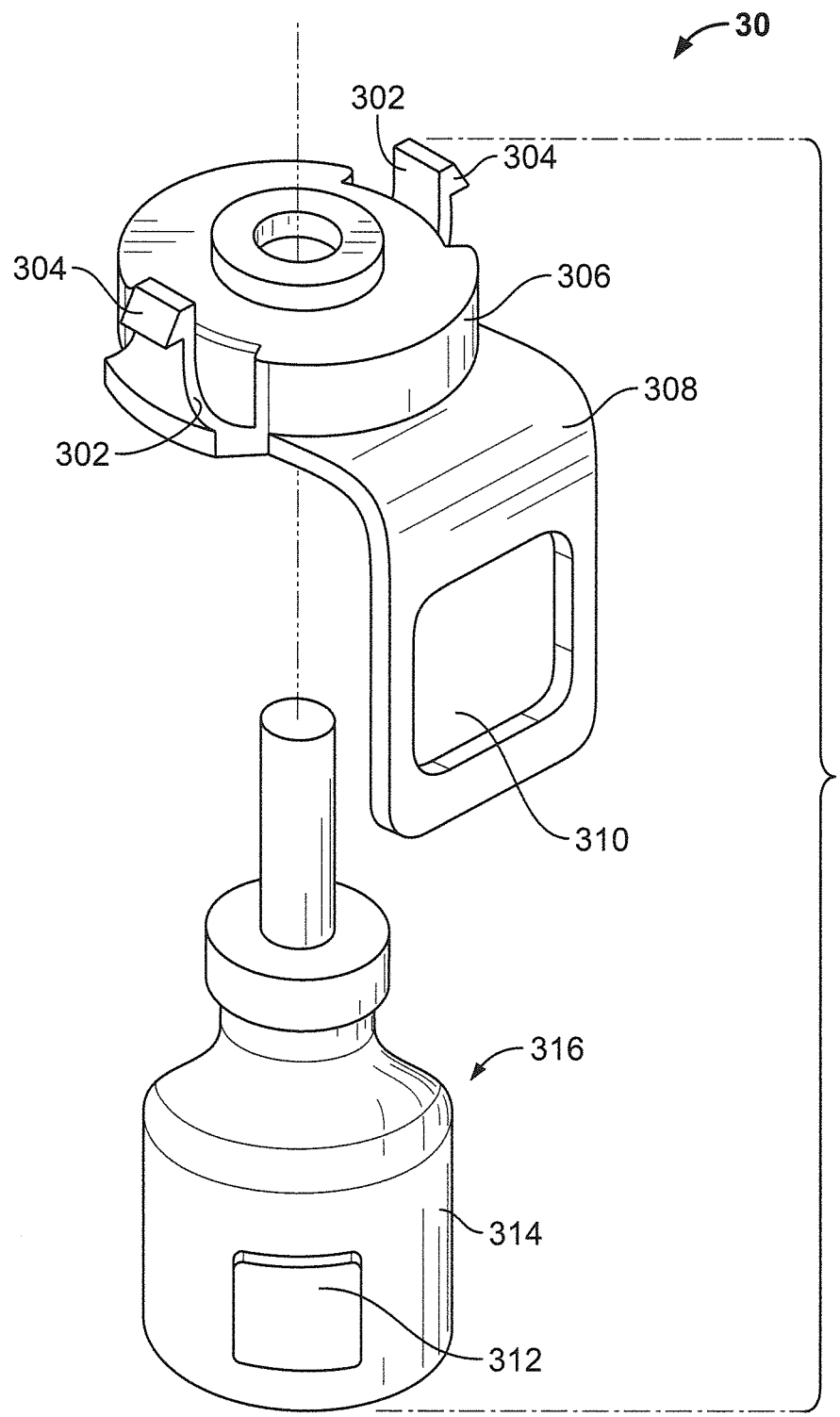
FIG. 11 is a top isometric view of a further embodiment of an adapter.

Still further embodiments of the adapters 32, 98 are envisioned, wherein the adapters 32, 98 include one or more features that prevent a neck portion of any refill (compatible or incompatible) from being retained by the latches 36 of the dispenser, but further include one or more additional features that retain the compatible refill, but not the incompatible refill. For example, in one embodiment as seen in FIG. 11, an adapter 300 is similar to the adapter 98 of FIGS. 7-10. In particular, the adapter 300 includes latches 302 with outwardly extending projections 304 that lock the adapter 300 into the dispenser 20 in the same manner as the adapter 98 of FIGS. 7-10. The adapter 300 includes a central neck portion 306 having no threading or other attachment mechanism on an inner surface thereof such that no refills (compatible or incompatible) can be attached to the neck portion 306 thereof. Optionally, other features can be utilized to lock out one or more refills. The adapter 300 includes a wall 308 curving outwardly and extending downwardly from the neck portion 306. The wall 308 includes an aperture 310 therethrough that corresponds to a shape of a projection 312 extending outwardly from a surface 314 of a compatible refill 316. The aperture 310 and projection 312 may have any shape(s) and may be complementary or non-complementary, as long as the aperture 310 accepts the projection 312 therein and retains the compatible refill 316 within the adapter 300. In such embodiment, incompatible refills with no projections extending therefrom or projections incapable of cooperating with the aperture 310 extending therefrom cannot be attached thereto.

Figure 12:
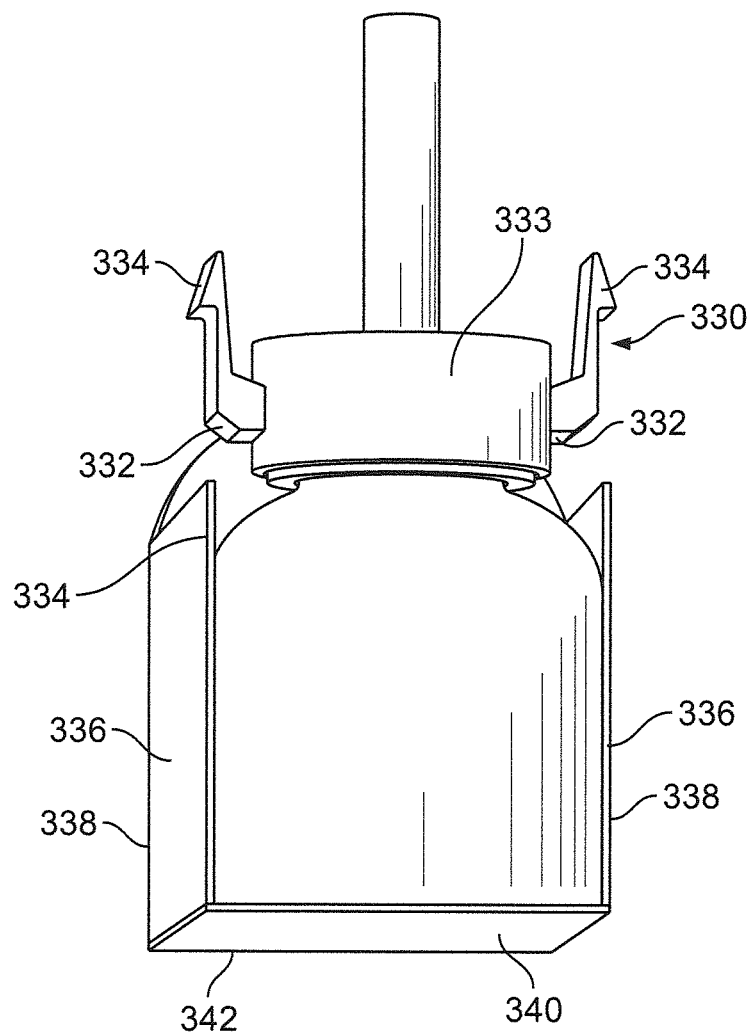
FIG. 12 is a top isometric view of yet another embodiment of an adapter.

FIG. 12 is a further embodiment of an adapter 330 in which one or more features prevent a neck portion of any refill (compatible or incompatible from being retained by the latches 36 of the dispenser 20, but further includes one or more additional features that retain the compatible refill, but not the incompatible refill. In particular, the adapter 330 includes latches 332 with outwardly extending projections 304 that lock the adapter 330 into the dispenser 20 in the same manner as the adapter 98 of FIGS. 7-10. The adapter 330 includes a central neck portion 333 having no threading or other attachment mechanism on an inner surface thereof such that no refills (compatible or incompatible) can be attached to the neck portion 333 thereof. Optionally, other features can be utilized to lock out one or more refills. The adapter 330 includes a wall 334 extending outwardly and downwardly therefrom, wherein the adapter 330 further includes one or more walls 336 extending outwardly from side edges 338 of the wall 334 and/or a shelf 340 extending outwardly from a bottom edge 342 of the wall 334. The one or more walls 336 and/or the shelf 340 allow for retention of a compatible refill 342 within the confines of the one or more walls 336 and/or the shelf 340 and prevent retention of an incompatible refill therein. Prevention of retention of an incompatible refill occurs due to the different dimensions of the incompatible refill as compared to the compatible refill.

The dispensers employing the refills described herein may comprise a variety of forms as known in the art. The dispensers may optionally use electric power in the form of batteries or an electrical plug during the operation thereof. The dispensers also optionally may include one or more of a heater, a fan, and/or other diffusion elements disposed in a housing that help facilitate the release of the volatile active. The dispensers may further include one or more openings in the housing to allow the volatile material to be dispensed from the housing to the surrounding environment. In place of the latches 28A, 2813, the housing 22 may include a variety of internal implements or couplings to help secure the various refill bottles disclosed herein, such as, for example, snaps, ridges, undercuts, lips, notches, projections, grooves, interference fit, threading, and/or any other attachment methods known in the art. The dispenser may optionally accommodate one or more refills and may operate using a variety of timing sequences as known in the art.

Any of the embodiments described herein may be modified to include any of the structures or methodologies disclosed in connection with other embodiments.

INDUSTRIAL APPLICABILITY

The present invention provides a volatile material dispenser that is adapted for use with only compatible volatile material refills. In particular, an adapter that can be removably attached to the refill is inserted into the dispenser and retained thereby to prevent incompatible refills from being coupled or attached to the dispenser.

Numerous modifications to the present disclosure will be apparent to those skilled in the art in view of the foregoing description. Accordingly, this description is to be construed as illustrative only and is presented to enable those skilled in the art to make and use the disclosure and to teach the best mode of carrying out same. The exclusive rights to all modifications that come within the scope of the appended claims are reserved.

We claim:
1. A volatile material dispenser, comprising:
a housing;
a retention mechanism coupled to the housing;
a compatible volatile material refill that includes a first set of dimensions, a body, and a wick disposed within and extending out of the body; and
an adapter removably attached to the body of the compatible volatile material refill,
wherein the retention mechanism non-removably retains the adapter to the housing when the compatible volatile material refill and adapter combination are inserted therein,
and wherein when the compatible volatile material refill is removed from the adapter and the adapter is left within the housing of the volatile material dispenser, the adapter prevents incompatible volatile material refills having a second set of dimensions different from the first set of dimensions from being attached to the housing.

2. The volatile material dispenser of claim 1, wherein the retention mechanism includes walls that are disposed within the housing, wherein each wall terminates in a latch.

3. The volatile material dispenser of claim 2, wherein each wall further defines a notch disposed proximate each latch, and wherein the adapter is configured to be retained within the notches by the latches.

4. The volatile material dispenser of claim 1, wherein the incompatible volatile material refill could be retained by the retention mechanism but for the presence of the adapter.

5. The volatile material dispenser of claim 1, wherein the retention mechanism is configured to fracture if the adapter is forcibly removed from the housing.

6. The volatile material dispenser of claim 1, wherein the adapter is a substantially semi-circular structure with opposing resilient outwardly facing C-shaped clasps.

7. The volatile material dispenser of claim 1, wherein the adapter further includes one or more grooves or projections on an inner surface thereof that are configured to correspond to a threaded portion, projections, or grooves on the compatible volatile material refill.

8. The volatile material dispenser of claim 1, wherein the adapter includes upwardly extending latches that terminate in outwardly extending projections.

9. The volatile material dispenser of claim 8, wherein the retention mechanism further include walls disposed within the housing that define gaps, and wherein the latches of the adapter are inserted into the gaps so that the outwardly extending projections prevent the adapter from being removed from the housing.

10. A method of preventing retention of an incompatible bottle to a volatile material dispenser, the method comprising the steps of:
providing a first bottle having a first set of dimensions, a reservoir portion with a volatile material therein, a neck portion extending upwardly from the reservoir portion, and a wick in contact with the volatile material and extending out of the bottle through the neck portion;
providing an adapter removably attached to the neck portion of the first bottle;
providing a volatile material dispenser including a housing and a retention mechanism;
inserting the first bottle with the adapter into a cavity within the housing so that the retention mechanism fixedly retains the adapter within the cavity of the housing;
detaching the first bottle from the adapter; and
preventing a second bottle from being attached to the volatile material dispenser by the adapter, wherein the second bottle has a second set of dimensions different from the first set of dimensions.

11. The method of claim 10, wherein the retention mechanism includes walls that are disposed within the housing, wherein each wall terminates in a latch.

12. The method claim 11, wherein each wall further defines a notch disposed proximate each latch, and wherein the adapter is retained within the notches by the latches.

13. The method of claim 10, wherein the second bottle could be retained by the retention mechanism but for the presence of the adapter.

14. The method of claim 10, wherein the adapter further includes one or more grooves or projections on an inner surface thereof that are configured to correspond to a threaded portion, projections, or grooves on the first bottle.

15. The method of claim 10, wherein the adapter includes upwardly extending latches that terminate in outwardly extending projections and the retention mechanism further includes walls disposed within the housing that define gaps, and wherein the latches of the adapter are inserted into the gaps so that the outwardly extending projections prevent the adapter from being removed from the housing.

16. A method of preventing retention of an incompatible bottle to a volatile material dispenser, the method comprising the steps of:
providing a volatile material dispenser including a retention mechanism, wherein the volatile material dispenser is adapted for use with a compatible volatile material refill that includes a bottle having a first set of dimensions, a body, and a wick disposed within and extending out of the body;
providing an adapter that is removably attached to the body of the bottle prior to insertion of the refill and the adapter into a cavity within a housing of the volatile material dispenser;
non-removeably coupling the adapter within the cavity by the retention mechanism; and
preventing an incompatible volatile material refill from being attached to the volatile material dispenser when the refill is removed therefrom and the adapter remains within the cavity within the volatile material dispenser, wherein the incompatible volatile material refill has a second set of dimensions different from the first set of dimensions.

17. The method of claim 16, wherein the retention mechanism includes walls that are disposed within the housing, wherein each wall terminates in a latch and further defines a notch disposed proximate each latch, and wherein the adapter is retained within the notches by the latches.

18. The method of claim 16, wherein the incompatible volatile material refill could be retained by the retention mechanism but for the presence of the adapter.

19. The method of claim 16, wherein the adapter further includes one or more grooves or projections on an inner surface thereof that are configured to correspond to a threaded portion, projections, or grooves on the compatible volatile material refill.

20. The method of claim 16, wherein the adapter includes upwardly extending latches that terminate in outwardly extending projections and the retention mechanism further include walls disposed within the housing that define gaps, and wherein the latches of the adapter are inserted into the gaps so that the outwardly extending projections prevent the adapter from being removed from the housing.

* * * * *